US00PP36711P2

(12) United States Plant Patent
Boxriker

(10) Patent No.: US PP36,711 P2
(45) Date of Patent: May 27, 2025

(54) ***DIANTHUS* PLANT NAMED 'KLEDG24541'**

(50) Latin Name: ***Dianthus caryophyllus* L.**
Varietal Denomination: KLEDG24541

(71) Applicant: KLEMM + SOHN GMBH & CO. KG, Stuttgart (DE)

(72) Inventor: Maike Boxriker, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/665,369

(22) Filed: May 15, 2024

(51) Int. Cl.
*A01H 5/02* (2018.01)
*A01H 6/30* (2018.01)

(52) U.S. Cl.
USPC ..... Plt./276

(58) Field of Classification Search
USPC ..... Plt./272, 276
See application file for complete search history.

(56) References Cited

U.S. PATENT DOCUMENTS

PP34,469 P2 * 8/2022 Thiede ..... A01H 6/305 Plt./281

* cited by examiner

*Primary Examiner* — Karen M Redden
*Assistant Examiner* — Zachariah Allan Kay
(74) *Attorney, Agent, or Firm* — Weatherly IP Solutions LLC; James M. Weatherly

(57) ABSTRACT

A new *Dianthus* plant designated 'KLEDG24541' particularly distinguished by bi-colored light pink and salmon colored flowers with a compact and upright growth habit, is disclosed.

1 Drawing Sheet

Genus and species: *Dianthus caryophyllus* L.
Variety denominations: 'KLEDG24541'.0

BACKGROUND

The present invention comprises a new and distinct variety of *Dianthus*, botanically known as *Dianthus caryophyllus* L, and hereinafter referred to by the variety name 'KLEDG24541'. 'KLEDG24541' originated from a whole plant mutation from the *Dianthus* line 'KLEDP07089' (unpatented) that was discovered in May 2020 in a greenhouse in Stuttgart, Germany.

In September 2020, 'KLEDG24541' was first vegetatively propagated by vegetative stem cuttings in Stuttgart, Germany. 'KLEDG24541' was found to reproduce true to type in successive generations of asexual propagation in Stuttgart, Germany via vegetative stem cuttings.

SUMMARY

The following are the most outstanding and distinguishing characteristics of 'KLEDG24541' when grown under normal horticultural practices in Stuttgart, Germany.

1. Bi-colored light pink and salmon colored flowers; and
2. A compact and upright growth habit.

DESCRIPTION OF THE PHOTOGRAPH

The new *Dianthus* plant provided herein is illustrated by the accompanying photograph taken in a greenhouse in Stuttgart, Germany, where the photograph shows a whole plant of the new *Dianthus* plant showing the foliage, buds and flower of a 11-week-old plant taken in March 2023. The colors shown are as true as can be reasonably obtained by conventional photographic procedures.

DESCRIPTION

The following detailed descriptions set forth the distinctive characteristics of 'KLEDG24541'. The data which define these characteristics were collected from asexual reproductions carried out in Stuttgart, Germany. Data was collected in April 2024 on a plant that was potted in week 41 of 2023. Color references are to The R.H.S. Colour Chart of The Royal Horticultural Society of London (R.H.S.), 5$^{th}$ edition (2007).

Classification:
*Family.*—Caryophyllaceae.
*Botanical.*—*Dianthus caryophyllus* L.
*Common.*—Pot carnation.
*Designation.*—'KLEDG24541'.

Parentage:
*Mutation parent.*—'KLEDP07089'.

Plant:
*Propagation type.*—Vegetative cuttings.
*Time to produce a rooted young plant.*—28 days.
*Root description.*—Fine roots, RHS 155C.
*Rooting habit shape.*—Lanceolate.
*Plant form.*—Upright.
*Plant height.*—12.0 cm.
*Plant diameter or spread.*—17.0 cm.

Lateral branches/stems:
*Shape of the branch in cross-section.*—Circular.
*Hollowness of the branch.*—Absent.
*Length.*—14.0 cm.
*Diameter.*—0.2 cm.
*Internode length.*—2.0 cm.

*Internode quantity per branch.*—4.
*Number of internodes per branch/stem.*—4.
*Node length.*—0.3 cm.
*Node diameter.*—0.5 cm.
*Texture.*—Smooth.
*Color.*—RHS 144A.
*Flower clustering on the lateral branch.*—In some lateral branches.

Foliage:
*Arrangement.*—Opposite.
*Length.*—5.9 cm.
*Width.*—0.8 cm.
*Shape.*—Obovate.
*Apex.*—Acute.
*Base.*—Obtuse.
*Margin.*—Entire.
*Texture (both upper and lower surfaces).*—Smooth.
*Cross-section of the leaf.*—Moderately concave.
*Curvature of the leaf.*—Absent.
*Glaucosity of the leaf.*—Weak.
*Leaf color (both immature and mature).*—Immature: Upper surface: RHS N137A. Lower surface: RHS N137C. Mature: Upper surface: RHS N137A. Lower surface: RHS N137D.
*Venation pattern.*—Absent.
*Venation color.*—Upper surface: RHS N137A. Lower surface: RHS N137D.

Flowers:
*Flower type and habit.*—Double sprays; and round.
*Fragrance.*—Present.
*Position of the flowers compared to the foliage of the plant.*—Same level.
*Profile of both the upper and lower part in the lateral view.*—Flat convex.
*Diameter of the flower.*—5.0 cm.
*Natural flowering season.*—Spring to autumn.
*Number of flowers per spray.*—2 to 5.
*Flower longevity on the plant.*—14 days.

Buds:
*Length.*—2.1 cm.
*Diameter.*—0.9 cm.
*Shape.*—Oblong.
*Color.*—RHS 137A.
*Extrusion of the styles at the bud stage.*—Absent.

Corolla:
*Quantity of petals and arrangement.*—22.
*Corolla height.*—1.8 cm.
*Petal length.*—3.4 cm.
*Petal width.*—1.8 cm.
*Petal shape.*—Obtuse.
*Petal apex.*—Obtuse.
*Petal base.*—Acute.
*Petal margin.*—Crenate.
*Depth of petal margin.*—Shallow.
*Petal texture (both upper and lower surfaces).*—Smooth.
*Petal color.*—Immature: Upper surface: RHS 73B margin and RHS 52A. Lower surface: RHS 65A. Mature: Upper surface: RHS 75C margin and RHS 52A. Lower surface: RHS 65C.
*Macule.*—Absent.

Calyx:
*Quantity of sepals and arrangement.*—Composed of 5 sepals.
*Longitudinal axis of the lobes of the calyx.*—Straight.
*Shape.*—Acute.
*Calyx height.*—2.3 cm.
*Calyx diameter (at the apex).*—1.3 cm.
*Sepal texture (both upper and lower surfaces).*—Smooth.
*Sepal color.*—Upper surface: RHS 137B. Lower surface: RHS 145A.
*Position of the outer lobes of the epicalyx in relation to the calyx.*—Adpressed and free.
*Apex shape of the outer lobes of the epicalyx.*—Acute.
*Tip length of the outer lobes of the epicalyx.*—0.3 cm.
*Apex shape of the inner lobes of the epicalyx.*—Short acuminate.
*Tip length of the inner lobes of the epicalyx.*—0.5 cm.

Peduncles:
*Length.*—1.5 cm.
*Diameter.*—0.2 cm.
*Strength.*—Strong.
*Texture.*—Smooth.
*Color.*—RHS N137A.

Reproductive organs:
*Stamens.*—Quantity per flower: 4 to 5. Filament length: 1.8 cm. Filament color: RHS 145A. Anther length: 0.2 cm. Anther diameter: 0.1 cm. Anther color: RHS 56D. Pollen amount: None observed.
*Pistils.*—Quantity per flower: 2. Length: 0.5 cm. Diameter: 0.1 cm. Stigma: Color: RHS 61C. Shape: Filamentous. Length: 0.2 cm. Diameter: 0.1 cm. Style: Color: RHS 155A. Length: 0.5 cm. Diameter: 0.1 cm. Ovary: Color: RHS 145B. Width: 0.7 cm.

Seeds: None observed to date.

Disease and insect resistance: No particular disease or insect resistance observed.

COMPARISON WITH PARENTAL LINE AND KNOWN VARIETY

'KLEDG24541' is distinguished from the parental line as described in Table 1.

TABLE 1

Comparison with Parental Line

| Trait or characteristic | 'KLEDG24541' | Female parent |
|---|---|---|
| Flower color | Bi-colored light pink and salmon red | Pink to purple |

'KLEDG24541' can be compared to the commercial *Dianthus* variety 'KLEDP07088' (not patented). Differences between the varieties are described in Table 2.

TABLE 2

Comparison with Similar Variety

| Characteristic | 'KLEDG24541' | 'KLEDP07088' |
|---|---|---|
| Flower color | Bi-colored light pink and salmon red | Purple with pattern |
| Growth Habit | Compact Upright | Medium Semiupright |

I claim:

1. New and distinct variety of *Dianthus* plant designated 'KLEDG24541', as illustrated and described herein.

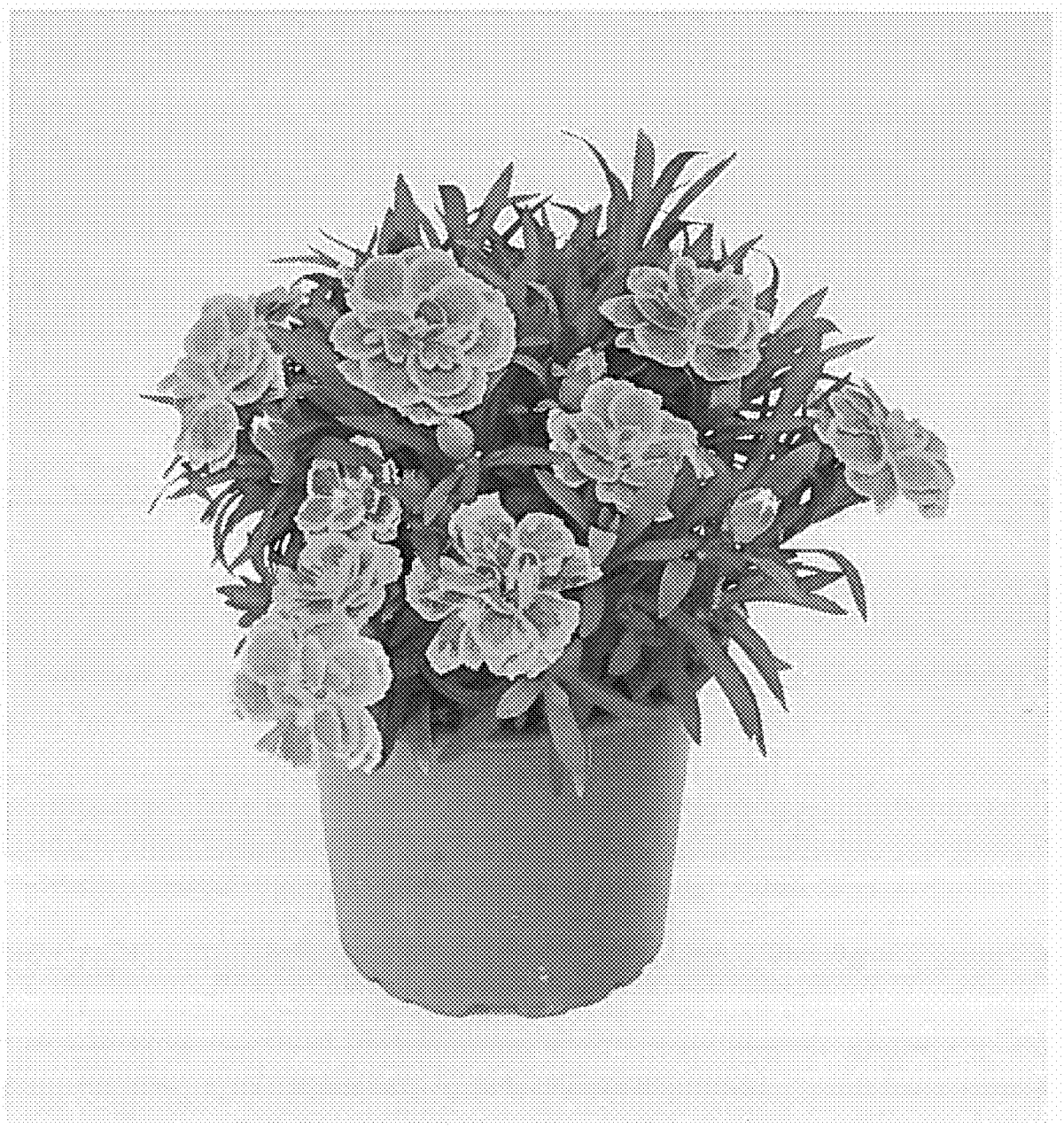

* * * * *